US011435335B2

United States Patent
Ly et al.

(10) Patent No.: US 11,435,335 B2
(45) Date of Patent: Sep. 6, 2022

(54) METHODS AND DEVICES CORRELATING WELL-LOGS TO CUTTINGS LITHOLOGIES FOR SYNTHETIC CORE GENERATION

(71) Applicant: CGG SERVICES SAS, Massy (FR)

(72) Inventors: Chi Vinh Ly, Houston, TX (US); Ross Taylor, Katy, TX (US)

(73) Assignee: CGG SERVICES SAS, Massy (FR)

( * ) Notice: Subject to any disclaimer, the term of this patent is extended or adjusted under 35 U.S.C. 154(b) by 40 days.

(21) Appl. No.: 16/913,349

(22) Filed: Jun. 26, 2020

(65) Prior Publication Data

US 2021/0405014 A1    Dec. 30, 2021

(51) Int. Cl.
*G01N 33/24* (2006.01)
*G06K 9/62* (2022.01)
(Continued)

(52) U.S. Cl.
CPC .......... *G01N 33/24* (2013.01); *E21B 49/005* (2013.01); *G01N 23/2251* (2013.01); *G01V 1/40* (2013.01); *G06K 9/6201* (2013.01); *G06T 7/40* (2013.01); *E21B 21/066* (2013.01); *E21B 2200/20* (2020.05); *G01N 2223/07* (2013.01); *G01N 2223/507* (2013.01); *G01V 2210/6224* (2013.01); *G01V 2210/6226* (2013.01);
(Continued)

(58) Field of Classification Search
CPC .............. G01N 33/24; G01N 23/2251; G01N 2223/07; G01N 2223/507; E21B 49/005; E21B 2200/20; E21B 21/066; G01V 1/40; G01V 2210/6224; G01V 2210/6226; G01V 2210/6246; G06K 9/6201; G06T 7/40; G06T 2207/20081; G06T 2207/30181

See application file for complete search history.

(56) References Cited

U.S. PATENT DOCUMENTS

| 2013/0292111 A1* | 11/2013 | Euzen | G01V 11/002 166/250.01 |
| 2014/0025301 A1* | 1/2014 | Storm, Jr. | G01V 11/00 702/6 |

(Continued)

OTHER PUBLICATIONS

Moscariello, Andrea, et al. "Sequence stratigraphy and reservoir characterisation of barren fluvial sequences using rock-typing analyses of core and cuttings." GEO 2010. European Association of Geoscientists & Engineers, 2010. (Year: 2010).*

(Continued)

*Primary Examiner* — Vu Le
*Assistant Examiner* — Tracy Mangialaschi
(74) *Attorney, Agent, or Firm* — Patent Portfolio Builders PLLC (57) ABSTRACT

An exploration method starts from cuttings associated with sampling intervals and well data for a well in a subsurface formation. The cuttings are prepared and analyzed to extract textural and chemical/mineralogical data for plural fragments in each sample that is made of the cuttings in one sampling interval. The method then includes matching lithotypes of rock defined according to the textural and chemical/mineralogical data for each fragment with segments of the well data in the corresponding sampling interval to obtain correspondences between the lithotypes and depth ranges. The correspondences between the lithotypes and the depth ranges may be used as constraints for seismic data inversion.

20 Claims, 7 Drawing Sheets

(51) Int. Cl.
*G01N 23/2251* (2018.01)
*G01V 1/40* (2006.01)
*E21B 49/00* (2006.01)
*G06T 7/40* (2017.01)
*E21B 21/06* (2006.01)

(52) U.S. Cl.
CPC ............... *G01V 2210/6246* (2013.01); *G06T 2207/10061* (2013.01); *G06T 2207/20081* (2013.01); *G06T 2207/30181* (2013.01)

(56) References Cited

U.S. PATENT DOCUMENTS

| | | | | |
|---|---|---|---|---|
| 2015/0025863 | A1* | 1/2015 | Walls | G01N 33/241 |
| | | | | 703/2 |
| 2017/0131429 | A1* | 5/2017 | Schneider | E21B 21/01 |
| 2020/0284145 | A1* | 9/2020 | ElGamal | B07B 13/18 |

OTHER PUBLICATIONS

Moradi, Majid, Behzad Tokhmechi, and Pedram Masoudi. "Inversion of well logs into rock types, lithofacies and environmental facies, using pattern recognition, a case study of carbonate Sarvak Formation." Carbonates and Evaporites 34.2 (2019): 335-347. (Year: 2019).*

Sliwinski, Jon, Michael Le Strat, and Murray Dublonko. "A new quantitative method for analysis of drill cuttings and core for geologic, diagenetic and reservoir evaluation." AAPG Annual Convention and Exhibition, Denver, Colorado, USA. 2009. (Year: 2009).*

\* cited by examiner

METHODS AND DEVICES CORRELATING WELL-LOGS TO CUTTINGS LITHOLOGIES FOR SYNTHETIC CORE GENERATION

BACKGROUND

Technical Field

Embodiments of the subject matter disclosed herein generally relate to methods and systems for geological exploration, and, in particular, to methods and systems for correlating well-logs with cutting lithologies.

Discussion of the Background

Seismic surveys are performed over hydrocarbon-rich formations to acquire seismic data carrying structural information. Seismic data provides measurements of travel times of seismic waves from the source to various receivers. Seismic data processing is a type of inverse problem, that is, a model of the underground formation probed when seismic data was acquired is developed and perfected so that simulated data generated using the model and physical laws to match the seismic data as close as possible. The model is a three-dimensional (3D) image of the underground formation with "pixels colored" by various properties values throughout the underground formation's volume. The inversion results are usually not unique (i.e., more than one model may adequately fit the data) and may be sensitive to relatively small errors in data collection, processing, or analysis. For these reasons, integrating additional information such as petrophysical well logs provide a valuable tool for enhancing the outcome of seismic data processing. The subsurface formation's image serves for locating natural resources such as hydrocarbon reservoirs and planning their exploitation.

Thus, an inversion process applied to the seismic data yields or improves a model of the subsurface formation and estimated attribute values (e.g., elastic properties). The inversion results may be constrained to be consistent with attribute values obtained from vertical well log data and sample analysis. The seismic inversion may simultaneously yield plural elastic properties (e.g., P-impedance, S-impedance and density) values and may reconstruct both the overall structure and the fine structural details. Note that impedance is the product of density and wave propagation velocity, P-impedance referring to the faster primary compressional waves and S-impedance referring to secondary shear waves.

Using the 3D image resulting from the inversion has remained a challenge in terms of associating the property values measured and estimated (e.g., measured acoustic responses and modeled rock elastic properties) to actual rock types. Such associations have been attempted by cross plotting the elastic properties measured in the well logs, and clustering lithologies with similar acoustic responses. For less complex lithologies, these techniques are usually adequate for isolating and reducing the total number of lithotypes to a practical number for use in the seismic inversion process. However, in complex/heterolithic lithologies, as this approach fails, core data is employed to describe the complex lithologies and group/reduce rock types to practical numbers for seismic inversion. However, cores are expensive to extract, existing cores may have not sampled targeted horizons, or the large number of potential target formation makes coring impractical.

Cuttings are available as a source of direct geological evidence of rock types in the subsurface, however, cuttings resolution does not allow for definition of fine structures. Traditionally it has been considered that cuttings can only provide an average lithology over the interval sampled by the cuttings. Currently, there has not been any method to order the cutting litho-fragments back to their exact depth of sampling.

It is therefore desirable, to better constrain inversion of seismic data using structural information based on cutting analysis, the cutting being readily available, but conventionally not correlated with their sampling depth.

SUMMARY

Methods and devices according to various embodiments use analytical techniques of cuttings that provide both chemical, mineralogical and rock textural information, and correlation with well logs to order cuttings back to their depth of sampling. The cuttings are reordered such that a good replacement of core data to improve the inversion of seismic data and thereby better plan exploitation of natural resources therein.

According to an embodiment there is an exploration method including obtaining cuttings associated with sampling intervals and well data for a well in a subsurface formation, preparing and analyzing the cuttings to extract textural and chemical/mineralogical data for plural fragments in each sample made of the cuttings in one sampling interval, and matching lithotypes of rock defined according to the textural and chemical/mineralogical data for each fragment with segments of the well data in the respective sampling interval to obtain correspondences between the lithotypes and depth ranges.

According to another embodiment there is a sample-versus-well data cross-analysis computer having an interface and a processor connected to the interface. The interface is configured to obtain textural and chemical/mineralogical data for plural fragments in each sample made of cuttings associated with a sampling interval along a well in a subsurface formation. The processor is configured to match lithotypes of rock defined according to the textural and chemical/mineralogical data for each fragment, with segments of the well data in the respective sampling interval to obtain correspondences between the lithotypes and depth ranges.

According to yet another embodiment there is a computer readable recording medium storing executable codes which, when executed on a computer make the computer perform an exploration method. The method includes obtaining textural and chemical/mineralogical data for plural fragments in each sample made of cuttings associated with a sampling interval along a well in a subsurface formation, and matching lithotypes of rock defined according to the textural and chemical/mineralogical data for each fragment with segments of the well data in the respective sampling interval to obtain correspondences between the lithotypes and depth ranges.

BRIEF DESCRIPTION OF THE DRAWINGS

The accompanying drawings, which are incorporated in and constitute a part of the specification, illustrate one or more embodiments and, together with the description, explain these embodiments. In the drawings.

DETAILED DESCRIPTION

The following description of the exemplary embodiments refers to the accompanying drawings. The same reference numbers in different drawings identify the same or similar elements. The following detailed description does not limit the invention. Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places is not necessarily referring to the same embodiment. Further, the particular features, structures or characteristics may be combined in any suitable manner in one or more embodiments.

Embodiments described hereinafter use of data obtained from the analysis of cuttings. A cutting sample may have fragments of rocks originating from a span of 10-100 ft depth and therefore includes few lithotypes (in this document also called "families"). The well logs are used to correlate the families with depth along the well (i.e., more accurately than the sampling range of 10-30 ft).

Figure 1:
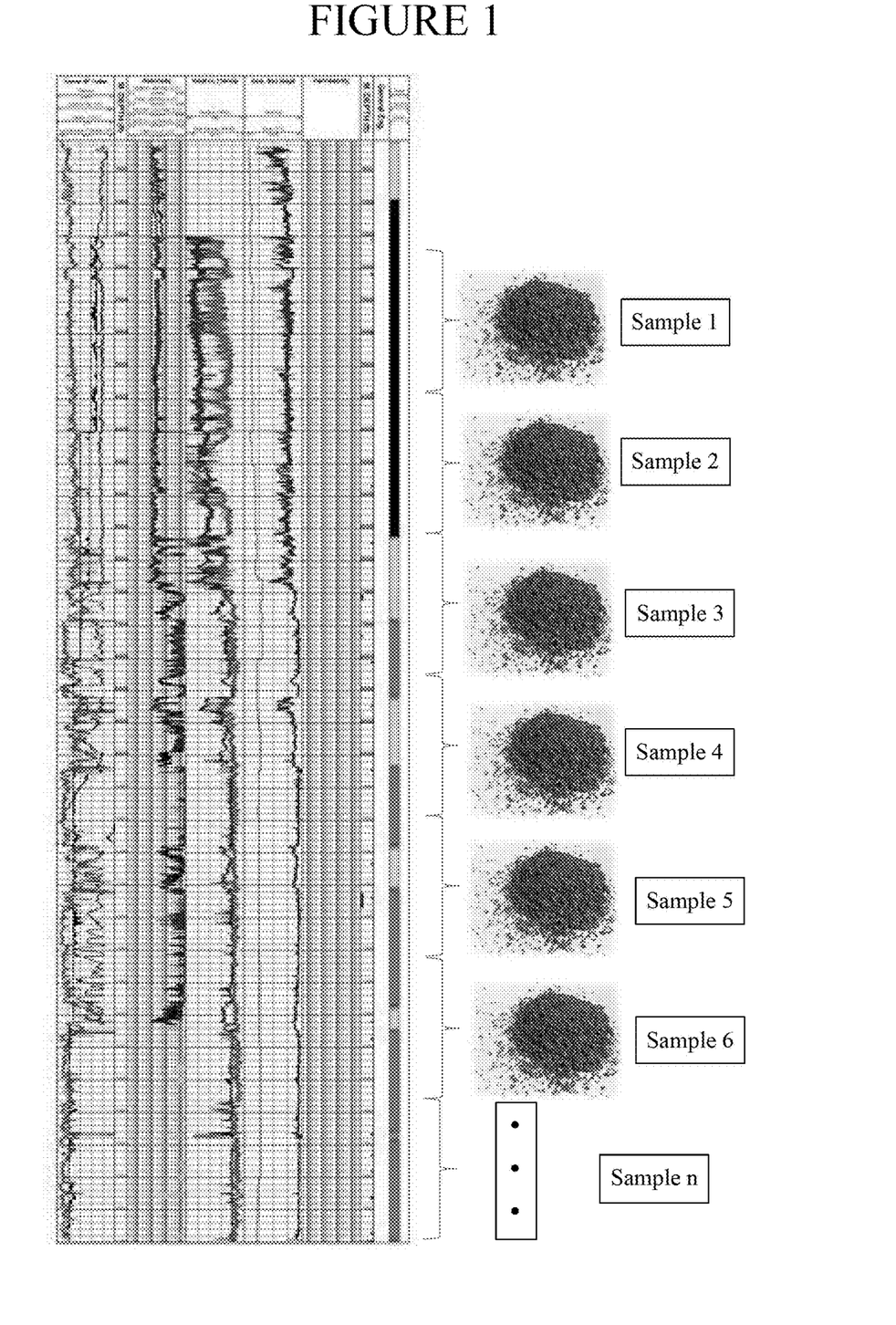
FIG. 1 shows cutting samples collected along a well (represented along a well log)

The cuttings are fragments of rock ejected from a borehole using together with a water or oil-based fluid. FIG. 1 shows cutting samples collected along a well (represented along a well log).

Figure 2:
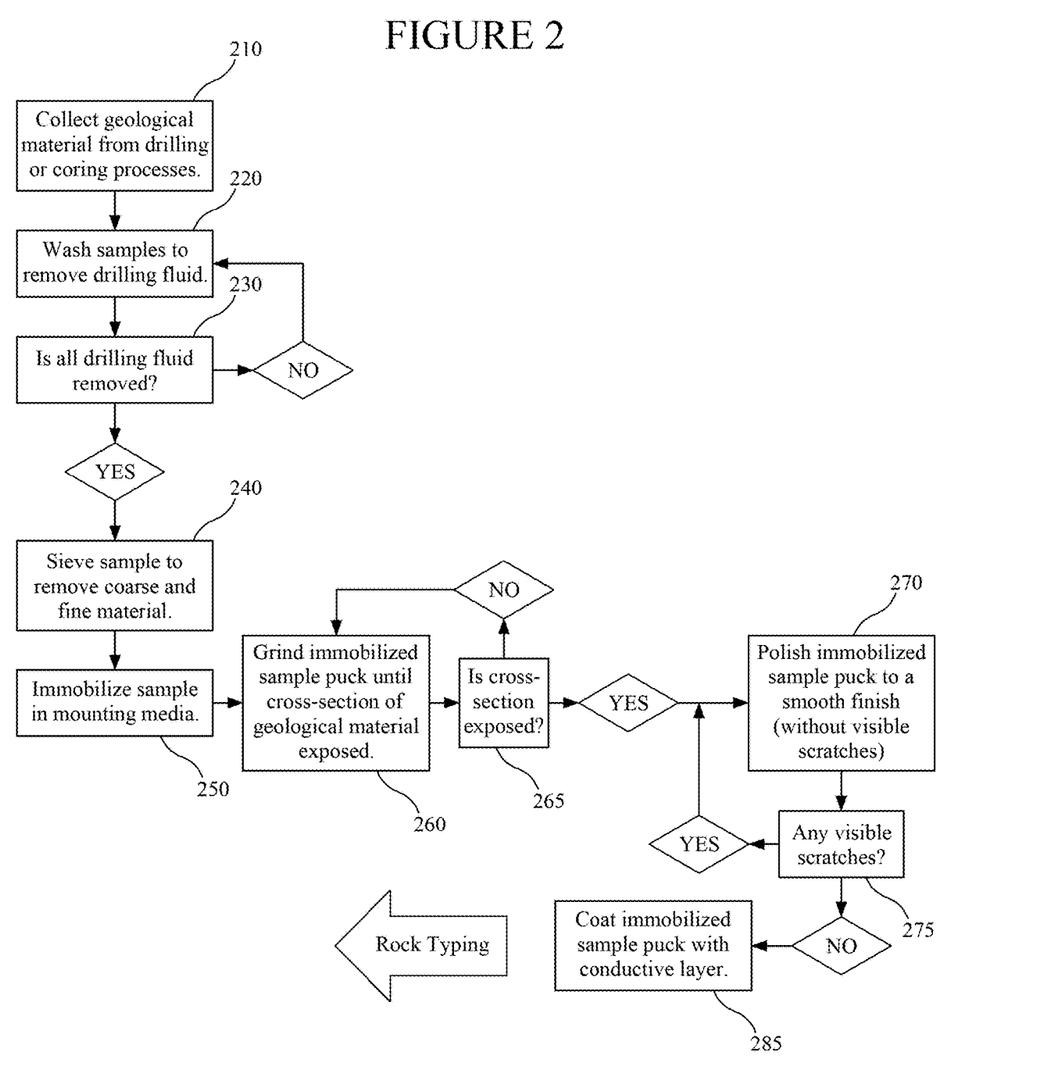
FIG. 2 a schematic representation of a preparation process performed for a cutting sample.

FIG. 2 a schematic representation of a preparation process performed for a cutting sample. The collected geological material 210 (i.e. cuttings) is cleaned at 220 using of petrochemical fluids and water, as well as other organic and inorganic solvents and detergents. The process by which the samples are cleaned follows accepted practice in the industry (e.g., until drilling fluid is removed at an acceptable degree as verified at 230). The drill cuttings are then passed through sieves to retain pieces of between a low size and a high size simit (e.g., 60 μm to 2 mm) at 240. For example, a coarse sieve is used to remove all pieces larger than the high size, known as "cave-in material." All the remaining material (with pieces smaller than accepted cave-in size) is further passed through a fine sieve designed to allow rock flour smaller than the low size to pass through. This remaining material is then prepared for analysis according to the requirements of the analysis instrument. For a scanning electron microscope (SEM), the pieces are immobilized in a suspension media, which could include polymerized plastic or resin, at 250, before a cross-sectional surface of one plane of the block is prepared such that geological fragments having different types to be exposed.

Figure 3:
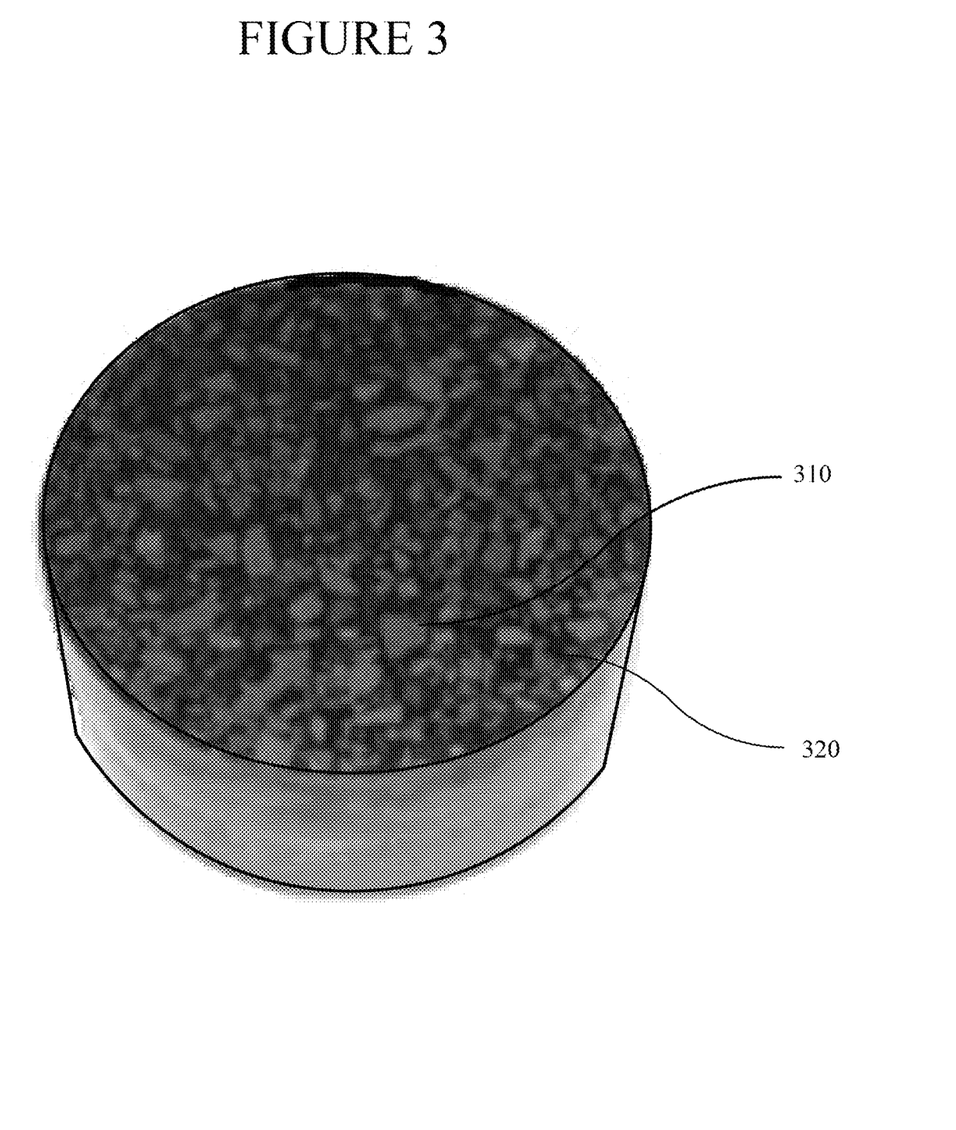
FIG. 3 illustrates a prepared sample.

Finishing operations 260, 270 and 280 then follow. At 260, a cross-section of the geological material is obtained on the immobilized sample puck is via mechanical or other removal (e.g., ion milling and laser cutting) of surface material—whether the operation is finished being verified at 265. At 270, a smooth finish is obtained on the surface of the immobilized sample puck via mechanical processes (condition that is verified at 275). Last, at 280, the immobilized sample puck is coated with a conductive layer. FIG. 3 shows an immobilized sample puck in which the cuttings such 310 have a lighter shade of gray than the suspension media 320.

Figure 4:
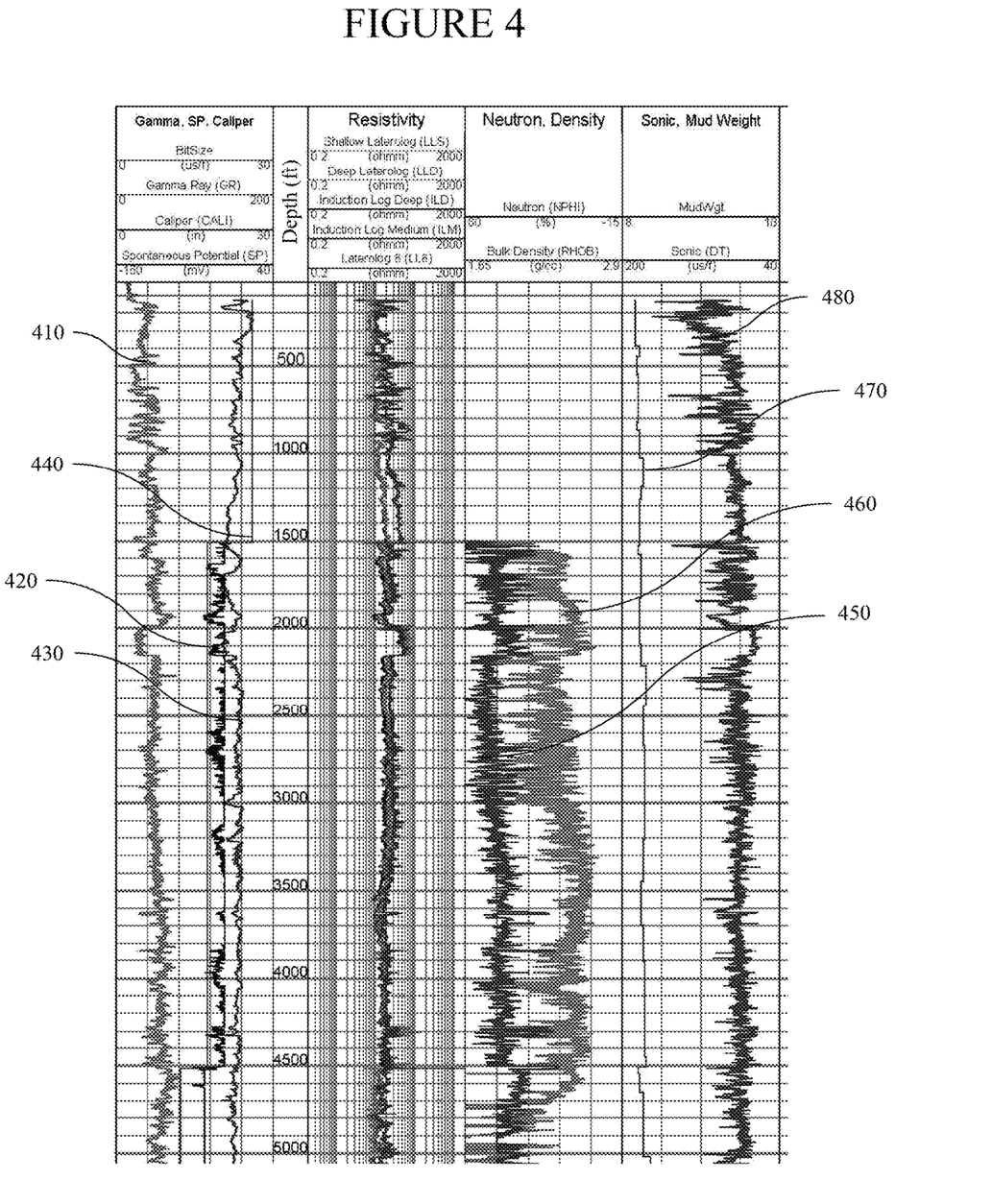
FIG. 4 illustrates well data.

As illustrated in FIG. 4, these samples are then subjected to an automated mineralogical (AM) analysis at 410, which involves scanning of a baryon/lepton beam over their surface and measuring the various scattered beams emerging from the sample's interactions with the baryon/lepton beam. In one embodiment, an incident baryon/lepton beam causes electromagnetic radiation, secondary generated leptons or baryons and a backscattered lepton beam. A detector is then use to measures secondary and backscattered lepton beams to image the sample. The image data is then used to determine such properties as particle size, grain size, porosity, particle and mineral angularity, particle and grain circularity and other textural features of the material. The electromagnetic radiation generated from the lepton beam interaction can be used to determine the spatial deposition of elements throughout the sample. The spatial elemental data can then be used to infer the mineralogical assemblage of the sample, and to generate either a spatially mapped mineralogical image of the sample, or a single bulk mineral composition of the sample. To summarize, the AM yields textural data 420 and chemical/mineralogical data for cutting fragments (particles) exposed on the prepared sample surface.

This primary data (i.e. the textural and chemical/mineralogical data) is then used to catalogue fragments into different families (i.e., lithotypes). Additionally, the shape and size of mineral grains within each fragment can also be used to further differentiate the families. The families may each be characterized by a geological rock type such as limestone, mudstone, wackestone, etc. and/or be further described based on the chemistry, mineralogy, shape and size of particles and grains. This process of analysis is performed sample by sample and repeated for each sample made of cuttings in different intervals to catalogue the fragments into the respective families.

Once the sample analysis is completed, the well logs over the sampling interval for each sample is examined to correlate the various log responses with the different families. Well logs are measurements acquired by lowering a string of instruments in a well recording petrophysical properties at different depths using a variety of sensors. Well logs include measurements of multiple properties: electrical, acoustic, stimulated radioactive responses, electromagnetic, nuclear magnetic resonance, pressure, etc. FIG. 4 illustrates a sample log which is now described in more detail.

The sample well log illustrated in FIG. 4 includes four sets of measurements illustrates in overlapping graphs with depth (in feet) that increases from top to bottom and is marked between the first and second overlapping graphs. The first overlapping graph (first one from the left) shows gamma ray measurement curve 410 in a range of $_{0-200}$ (GR), spontaneous potential in a range of −160 to 40 mV, caliper measurement 430 and bit size measurement 440 of the well diameter in a range of 0-30 in. The second overlapping graph illustrates different resistivity measurements (shallow, deep, induction, lateral) in a logarithmic scale for a range of 0.2-2000 Ω.m. The third overlapping graph illustrates neutron scattering log 450 calibrated to a porosity scale of up to 60% and a bulk density measurement 460 in the range of 1.65-2.9 g/cm$^3$. The fourth overlapping graph (first one from the right) illustrates a mud weight 470 measurement in a range of 8-18 and sonic 480 (i.e., travel time of sound through the rock) in a range of 40 to 200 μs/ft.

Figure 5:
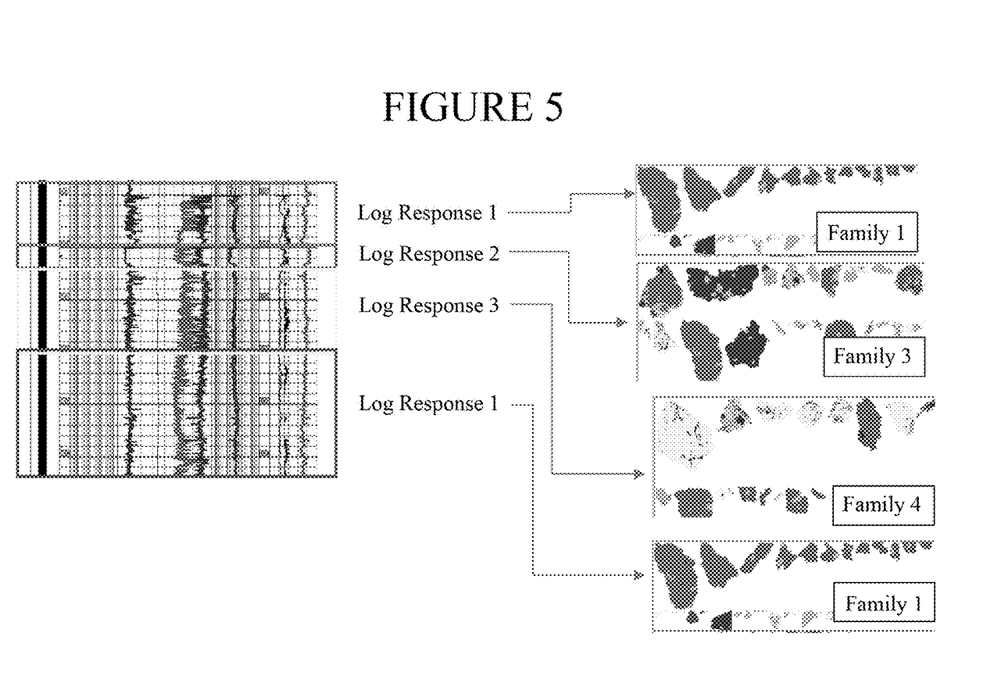
FIG. 5 illustrates the matching process according to an embodiment.

The families in each sampling interval are cross referenced against well log responses over the sampling interval;

the number and type of responses is then compared to similar log responses in other sampling intervals while also referencing the family types in these other intervals. This process of pattern matching log responses with families (or family types) may be implemented using pattern-recognition machine learning. Once a good correlation between log responses and families (or family types) is achieved, the cuttings in each sampling interval can be aligned with the log responses as determined by the pattern matching process as illustrated in FIG. 5.

Figure 6:
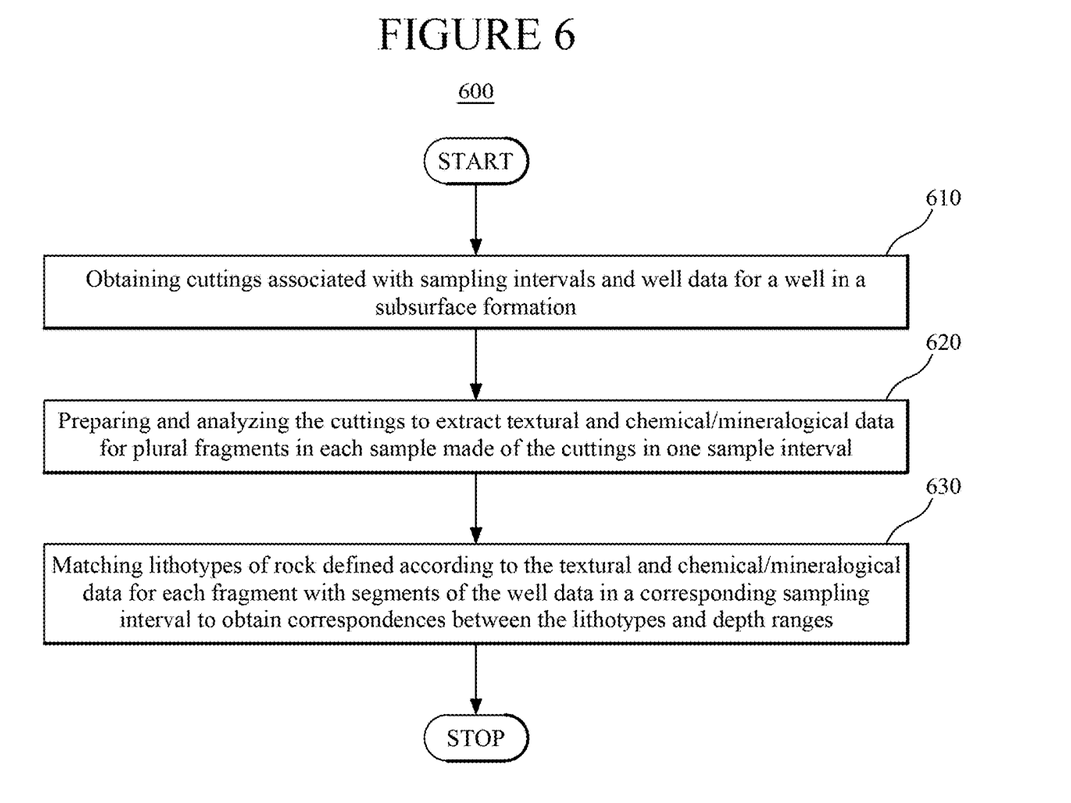
FIG. 6 is a flowchart according to an embodiment.

FIG. 6 is a flow chart of an exploration method 600 according to an embodiment. Method 600 includes obtaining cuttings associated with sampling intervals and well data for a well in a subsurface formation at 610. The well log data may include resistivity, permeability and density.

The sampling intervals may be between 10 and 100 ft, and the sampling interval of the well log data may be between 0.5 and 3 ft.

Method 600 further includes preparing and analyzing the cuttings to extract textural and chemical/mineralogical data for plural fragments in each sample made of the cuttings in one sample interval. The process of preparing samples for SEM has been described while referring to FIG. 2. However, this description is exemplary and should be not considered limiting. The analysis may be performed using a SEM but the use of this instrument is exemplarily not limiting.

Method 600 then includes matching lithotypes (i.e., families) of rock defined according to the textural and chemical/mineralogical data for each fragment with segments of the well data in a corresponding one of the sampling intervals to obtain correspondences between the lithotypes with depth ranges at 630. The correspondences between the lithotypes and the depth ranges may be used to generate constraints for seismic data inversion. The matching may use pattern-recognition machine learning.

The method may further include determining a presence of one of the lithotypes of rock in a depth range along the well without a cutting analysis, based on a portion of the well data corresponding to the depth range and results of the matching.

Figure 7:
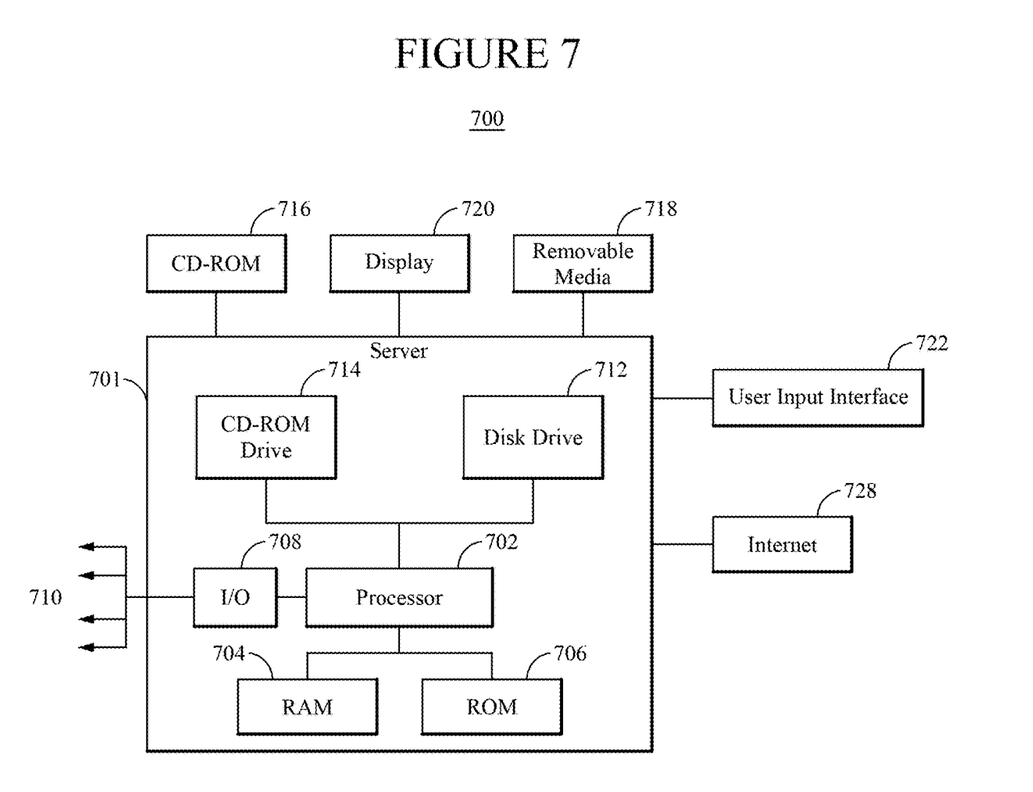
FIG. 7 is a schematic diagram of a computing device according to an embodiment.

The above-discussed methods may be implemented in a computing device 700 as illustrated in FIG. 7. Hardware, firmware, software or a combination thereof may be used to perform the various steps and operations described herein.

Exemplary computing device 700 suitable for performing the activities described in the exemplary embodiments may include a server 701. Server 701 may include a central processor (CPU) 702 coupled to a random-access memory (RAM) 704 and to a read-only memory (ROM) 706. ROM 706 may also be other types of storage media to store programs, such as programmable ROM (PROM), erasable PROM (EPROM), etc. Processor 702 may communicate with other internal and external components through input/output (I/O) circuitry 708 and bussing 710 to provide control signals and the like. Processor 702 carries out a variety of functions as are known in the art, as dictated by software and/or firmware instructions.

Server 701 may also include one or more data storage devices, including hard drives 712, CD-ROM drives 714 and other hardware capable of reading and/or storing information, such as DVD, etc. In one embodiment, software for carrying out the above-discussed steps may be stored and distributed on a CD-ROM or DVD 716, a USB storage device 718 or other form of media capable of portably storing information. These storage media may be inserted into, and read by, devices such as CD-ROM drive 714, disk drive 712, etc. Server 701 may be coupled to a display 720, which may be any type of known display or presentation screen, such as LCD, plasma display, cathode ray tube (CRT), etc. A user input interface 722 is provided, including one or more user interface mechanisms such as a mouse, keyboard, microphone, touchpad, touch screen, voice-recognition system, etc.

Server 701 may be coupled to other devices, such as sources, detectors, etc. The server may be part of a larger network configuration as in a global area network (GAN) such as the internet 728, which allows ultimate connection to various computing devices.

According to one embodiment, I/O circuitry 708 is configured to obtain textural and chemical/mineralogical data for plural fragments in each sample made of the cuttings in one sample interval, and processor 702 is configured to match lithotypes of rock defined according to the textural and chemical/mineralogical data for each fragment with segments of the well data in a corresponding one of the sampling intervals to obtain correspondences between the lithotypes and depth ranges.

In yet another embodiment, RAM 704 stores executable codes that, when executed make the I/O circuitry 708 to obtain textural and chemical/mineralogical data for plural fragments in each sample made of the cuttings in one sample interval, and processor 702 to match lithotypes of rock defined according to the textural and chemical/mineralogical data for each fragment with segments of the well data in a corresponding one of the sampling intervals to obtain correspondences between the lithotypes and depth ranges.

The disclosed embodiments provide methods and devices for identifying rock types along a well using cuttings and well logs. It should be understood that this description is not intended to limit the invention. On the contrary, the exemplary embodiments are intended to cover alternatives, modifications and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments may be practiced without such specific details.

Although the features and elements of the present embodiments are described in the embodiments in particular combinations, each feature or element can be used alone without the other features and elements of the embodiments or in various combinations with or without other features and elements disclosed herein. The methods or flowcharts provided in the present application may be implemented in a computer program, software or firmware tangibly embodied in a computer-readable storage medium for execution by a general-purpose computer or a processor.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:
1. An exploration method comprising:
obtaining cuttings associated with sampling intervals and well data for a well in a subsurface formation, the sampling intervals being larger than intervals at which well data is acquired along the well;

preparing and analyzing the cuttings to extract textural and chemical/mineralogical data for each sample puck made of the cuttings in one of the sampling intervals; and matching lithotypes of rock defined according to the textural and chemical/mineralogical data for each sample puck, with segments of the well data in the respective sampling interval; and determining one of the lithotypes of rock in a depth range without a cutting analysis, based on the well data corresponding to the depth range and results of the matching.

2. The method of claim 1, wherein the textural and chemical/mineralogical data is obtained using a scanning electron microscope.

3. The method of claim 1, wherein the correspondences between the lithotypes and the depth ranges are used to generate constraints for a seismic data inversion.

4. The method of claim 1, wherein the matching uses pattern-recognition machine learning.

5. The method of claim 1, wherein the sampling intervals along the well are between 10 and 100 ft, and the well data is acquired at an interval between 0.5 and 3 ft.

6. The method of claim 1, wherein the well data includes resistivity, permeability and density.

7. The method of claim 1, wherein the preparing of the cuttings includes one or more of:
  collecting geological material from drilling;
  removing drilling fluid by washing the geological material;
  sieving the geological material to remove coarse and fine material thereby retaining samples withing a predetermined range;
  immobilizing the geological material in mounting media to form the sample puck;
  grinding the sample puck to expose a cross-section of the geological material;
  polish the sample puck; and
  coat the sample puck with a conductive layer.

8. A sample-versus-well data cross-analysis computer comprising:
  an interface configured to obtain textural and chemical/mineralogical data for plural fragments in each sample made of cuttings associated with a sampling interval along a well in a subsurface formation, the sampling interval being larger than an interval at which well data is acquired along the well; and
  a processor connected to the interface and configured
    to match lithotypes of rock defined according to the textural and chemical/mineralogical data for each sample puck made of the cuttings in one of the sampling intervals, with segments of the well data in the sampling interval; and
    to determine one of the lithotypes of rock in a depth range without a cutting analysis, based on a portion of the well data corresponding to the depth range and results of the matching.

9. The sample-versus-well data cross-analysis computer of claim 8, wherein the textural and chemical/mineralogical data is obtained using a scanning electron microscope.

10. The sample-versus-well data cross-analysis computer of claim 8, wherein the correspondences between the lithotypes and the depth ranges are used to generate constraints for a seismic data inversion.

11. The sample-versus-well data cross-analysis computer of claim 8, wherein the processor uses pattern-recognition machine learning to match the lithotypes with the segments of the well data.

12. The sample-versus-well data cross-analysis computer of claim 8, wherein the sampling intervals along the well are between 10 and 100 ft, and the well data is acquired at an interval between 0.5 and 3 ft.

13. The sample-versus-well data cross-analysis computer of claim 8, wherein the well data includes resistivity, permeability and density.

14. The sample-versus-well data cross-analysis computer of claim 8, wherein the cuttings are prepare by a process that includes one or more of:
  collecting geological material from drilling;
  removing drilling fluid by washing the geological material;
  sieving the geological material to remove coarse and fine material thereby retaining samples withing a predetermined range;
  immobilizing the geological material in mounting media to form the sample puck;
  grinding the sample puck to expose a cross-section of the geological material;
  polish the sample puck; and
  coat the sample puck with a conductive layer.

15. A non-transitory computer readable recording medium storing executable codes which, when executed on a computer make the computer perform an exploration method comprising:
  obtaining textural and chemical/mineralogical data for plural fragments in each sample puck made of cuttings associated with a sampling interval along a well in a subsurface formation, the sampling interval being larger than an interval at which well data is acquired along the well;
  matching lithotypes of rock defined according to the textural and chemical/mineralogical data for each sample puck, with segments of the well data in the respective sampling interval; and
  determining one of the lithotypes of rock in a depth range without cutting analysis, based on the well data corresponding to the depth range and results of the matching.

16. The non-transitory computer readable recording medium of claim 15, wherein the textural and chemical/mineralogical data is obtained using a scanning electron microscope.

17. The non-transitory computer readable recording medium of claim 15, wherein the correspondences between the lithotypes and the depth ranges are used to generate constraints for a seismic data inversion.

18. The non-transitory computer readable recording medium of claim 15, wherein the matching uses pattern-recognition machine learning.

19. The non-transitory computer readable recording medium of claim 15, wherein the sampling intervals along the well are between 10 and 100 ft, and the well data is acquired at an interval between 0.5 and 3 ft.

20. The non-transitory computer readable recording medium of claim 15, wherein the sample puck is prepared from the cuttings by performing one or more of:
  collecting geological material from drilling;
  removing drilling fluid by washing the geological material;
  sieving the geological material to remove coarse and fine material thereby retaining samples withing a predetermined range;

immobilizing the geological material in mounting media to form the sample puck;
grinding the sample puck to expose a cross-section of the geological material;
polish the sample puck; and
coat the sample puck with a conductive layer.

\* \* \* \* \*